US 11,319,271 B2

(12) United States Patent
Miyake et al.

(10) Patent No.: US 11,319,271 B2
(45) Date of Patent: May 3, 2022

(54) PROCESS FOR PREPARING (9Z,11E)-9,11-HEXADECADIENAL

(71) Applicant: Shin-Etsu Chemical Co., Ltd., Tokyo (JP)

(72) Inventors: Yuki Miyake, Niigata (JP); Takeshi Kinsho, Niigata (JP); Ryo Komatsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/352,480

(22) Filed: Jun. 21, 2021

(65) Prior Publication Data

US 2021/0403403 A1  Dec. 30, 2021

(30) Foreign Application Priority Data

Jun. 24, 2020 (JP) .............................. JP2020-108527

(51) Int. Cl.
C07C 45/42 (2006.01)
C07C 41/48 (2006.01)

(52) U.S. Cl.
CPC .............. *C07C 45/42* (2013.01); *C07C 41/48* (2013.01)

(58) Field of Classification Search
CPC .................. C07C 45/42; C07C 41/48
See application file for complete search history.

(56) References Cited

U.S. PATENT DOCUMENTS 4,357,474 A   11/1982   Carney et al.

OTHER PUBLICATIONS

Batista-Pereira et al. "Electrophysiological Studies and Identification of Possible Sex Pheromone Components of Brazilian Populations of the Sugarcane Borer, *Diatraea saccharalis*" Verlag der Zeitschrift für Naturforschung, 57c:753-758 (2002).
Kalinova et al. "(11Z)-hexadec-11-enal enhances the attractiveness of Diatraea saccharalis main pheromone component in wind tunnel experiments" Journal of Applied Entomology, 129(2):70-74 (2005).
Santangelo et al. "Identification, Syntheses, and Characterization of the Geometric Isomers of 9,11-Hexadecadienal from Female Pheromone Glands of the Sugar Cane Borer Diatraea saccharalis" Journal of Natural Products, 65:909-915 (2002).
Tao et al. "Facile Synthesis of (Z,E)-9,11-Hexadecadienal, the Major Sex Pheromone Component of the Sugarcane Borer Diatraea saccharalis: An Efficient Strategy for Synthesis of (Z,E)-Dienic Pheromones" Synthetic Communications, 43(3)415-424 (2013).

*Primary Examiner* — Sikarl A Witherspoon
(74) *Attorney, Agent, or Firm* — Myers Bigel, P.A.

(57) ABSTRACT

The present invention provides a process for preparing (9Z,11E)-9,11-hexadecadienal of the following formula (4), the process comprising: subjecting (2E)-2-heptenal of the following formula (1) to a Wittig reaction with a triarylphosphonium 9,9-dialkoxynonylide compound of the following general formula (2), wherein Ar represents an aryl group that may be same with or different from each other, and $R^1$ and $R^2$ represent, independently of each other, a monovalent hydrocarbon group having 1 to 15 carbon atoms, or $R^1$ and $R^2$ may form together a divalent hydrocarbon group, $R^1$—$R^2$, having 2 to 10 carbon atoms to form a (5E,7Z)-16,16-dialkoxy-5,7-hexadecadiene compound of the following general formula (3), wherein $R^1$ and $R^2$ are as defined above; and hydrolyzing the (5E,7Z)-16,16-dialkoxy-5,7-hexadecadiene compound (3) to form (9Z,11E)-9,11-hexadecadienal (4).

2 Claims, No Drawings

PROCESS FOR PREPARING (9Z,11E)-9,11-HEXADECADIENAL

TECHNICAL FIELD

The present invention relates to a process for preparing (9Z,11E)-9,11-hexadecadienal.

BACKGROUND ART

Sugarcane borer (*Diatraea saccharalis*), which is one of the most important pests of sugarcane in the North, Central, and South America countries such as the United States, Cuba, Columbia, Argentine, and Brazil, is known to be difficult to control. For example, the world largest sugarcane-producing country, Brazil, suffers extensive damage by *Diatraea saccharalis* in the vast areas every year. Larvae of the pest invade into a central part of the stem and, therefore, insecticides cannot reach the larvae as to be less effective. Accordingly, biological control methods have been attracting attention, and utilization of sex pheromone substances is expected as one of them.

A main component of a sex pheromone of *Diatraea saccharalis* is reported to be a dienal compound, (9Z,11E)-9,11-hexadecadienal (see the following Patent Literature 1, and Non-Patent Literatures 1 and 2).

A process for preparing the hexadecadienal is described in the following Non-Patent Literature 3. The process comprises oxidizing a hydroxyl group of 11-[(tetrahydro-2H-pyran-2-yl)oxy]-2-undecyn-1-ol with manganese dioxide, forming an ene-yne backbone in a Wittig reaction, followed by hydroboration with dicyclohexylborane and deprotection of a tetrahydropyranyl group with p-toluenesulfonic acid (p-TsOH) in ethanol to synthesize (9Z,11E)-9,11-hexadecadien-1-ol, and oxidizing a hydroxyl group of the resulting (9Z,11E)-9,11-hexadecadien-1-ol with pyridinium dichromate (PDC).

Another process for preparing the hexadecadienal starting from acetylene and acrolein is described in the following Non-Patent Literature 4. Specifically, these starting materials, palladium(II) acetate, and lithium bromide are used to synthesize (4Z,6E)-7-bromo-4,6-heptadienal. A formyl group of the resulting (4Z,6E)-7-bromo-4,6-heptadienal is converted into dimethylacetal, followed by a coupling reaction using dichloro[1,3-bis(diphenylphosphino)propane]nickel(II), and hydrolysis of the dimethylacetal to obtain (4Z,6E)-4,6-undecadienal. Subsequently, a formyl group of the resulting (4Z,6E)-4,6-undecadienal is subjected to an addition reaction with (tetrahydropyranyloxy)pentylmagnesium bromide, followed by tosylation reaction of the hydroxyl group, reduction of the sulfonic ester formed from the tosylation reaction with lithium aluminum hydride in diethyl ether, and removal of the tetrahydropyranyl group to obtain (9Z,11E)-9,11-hexadecadien-1-ol. Then, the hydroxyl group of the resulting (9Z,11E)-9,11-hexadecadien-1-ol is oxidized with pyridinium chlorochromate (PCC).

LIST OF THE PRIOR LITERATURES

Patent Literature

[Patent Literature 1] U.S. Pat. No. 4,357,474 A

Non-Patent Literatures

[Non-Patent Literature 1] Arlene G. Correa et al., 2002, Z. Naturforsch. 57c: 753-758.

[Non-Patent Literature 2] B. Kalinova et al., 2005, J. Appl. Entomol. 129 (2): 70-74.

[Non-Patent Literature 3] C. Rikard Unelius et al., 2002, J. Nat. Prod. 65: 909-915.

[Non-Patent Literature 4] Yunhai Tao et al., 2013, Synthetic Communications. 43: 415-424.

Problems to be Solved by the Invention

The process described in Non-Patent Literature 3 uses diethyl ether, which has a low boiling point and is flammable and, therefore, is unfavorable for industrial application. The process comprises oxidation reactions with manganese dioxide and a chromium compound, PDC, both of which cause extremely high environmental hazard. The oxidation reactions often involve a danger of explosion. Accordingly, the process is difficult to implement in an industrial scale. Further, the process has a total yield as extremely low as 16% and comprises steps as many as five.

The process described in Non-Patent Literature 4 uses a palladium catalyst and a nickel catalyst, both of which are expensive, and requires an equivalent-excessive amount of an expensive lithium bromide in the first step, which makes the process uneconomical. The process uses ignitable lithium aluminum hydride, and comprises an oxidation reaction using a chromium compound, PCC, which causes extremely high environmental hazard. The oxidation reaction often involves a danger of explosion. Accordingly, the process is difficult to implement in an industrial scale. In addition, the process has a total yield as extremely low as 19% and comprises steps as many as eight.

SUMMARY OF THE INVENTION

The present invention has been made in the aforesaid circumstances, and aims to provide a process for efficiently preparing (9Z,11E)-9,11-hexadecadienal.

As a result of the intensive researches to overcome the aforesaid problems of the prior art, the present inventors have found that (2E)-2-heptenal is a useful intermediate for the preparation of (9Z,11E)-9,11-hexadecadienal. The present inventors have also found that it is possible to construct the geometry at the position 11 in an E-selective manner by utilizing the geometry of a carbon-carbon double bond of (2E)-2-heptenal, and to construct the stereo structure of the position 9 in a Z-selective manner in Wittig reaction, which gives (9Z,11E)-9,11-hexadecadienal in shorter steps, in a high yield, and in a high purity. Thus, the present inventors have completed the present invention.

According to one aspect of the present invention, there is provided a process for preparing (9Z,11E)-9,11-hexadecadienal of the following formula (4):

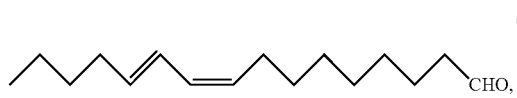
(4)

the process comprising:
subjecting (2E)-2-heptenal of the following formula (1):

(1)

to a Wittig reaction with a triarylphosphonium 9,9-dialkoxynonylide compound of the following general formula (2):

$$Ar_3P^+C^-H(CH_2)_7CH(OR^1)(OR^2) \quad (2)$$

wherein Ar represents an aryl group that may be same with or different from each other, and $R^1$ and $R^2$ represent, independently of each other, a monovalent hydrocarbon group having 1 to 15 carbon atoms, or $R^1$ and $R^2$ may form together a divalent hydrocarbon group, $R^1$-$R^2$, having 2 to 10 carbon atoms
to form a (5E,7Z)-16,16-dialkoxy-5,7-hexadecadiene compound of the following general formula (3):

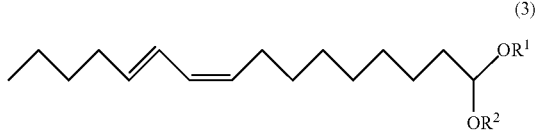

(3)

wherein $R^1$ and $R^2$ are as defined above; and
hydrolyzing the (5E,7Z)-16,16-dialkoxy-5,7-hexadecadiene compound (3) to form (9Z,11E)-9,11-hexadecadienal (4).

According to the present invention, it is possible to prepare (9Z,11E)-9,11-hexadecadienal (4) in a high yield and in shorter steps without relying on an oxidation reaction.

DETAILED DESCRIPTION OF THE
PREFERRED EMBODIMENTS

I. Preparation of the
(5E,7Z)-16,16-Dialkoxy-5,7-Hexadecadiene
Compound

A (5E,7Z)-16,16-dialkoxy-5,7-hexadecadiene compound of the following general formula (3), which is an intermediate for the preparation of the target compound of the present invention, (9Z,11E)-9,11-hexadecadienal, may be prepared by subjecting (2E)-2-heptenal of the following formula (1) to a Wittig reaction with a triarylphosphonium 9,9-dialkoxynonylide compound of the following general formula (2), as shown in the following chemical reaction formula.

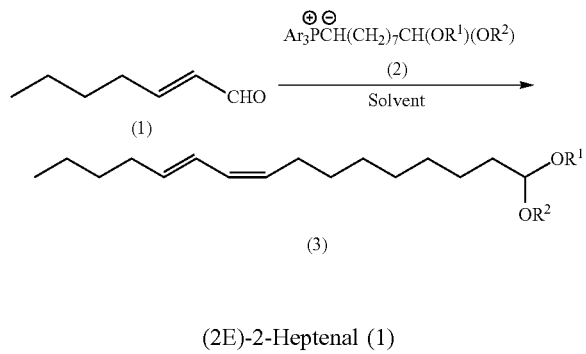

(2E)-2-Heptenal (1)

(2E)-2-Heptenal (1) may be commercially available one or may be prepared in house, for example, by oxidizing (2E)-2-hepten-1-ol or hydrolyzing (2E)-1,1-dialkoxy-2-heptene.

Triarylphosphonium 9,9-Dialkoxynonylide
Compound (2)

$R^1$ and $R^2$ in the general formula (2) represent, independently of each other, a monovalent hydrocarbon group having 1 to 15, preferably 1 to 6 carbon atoms, or $R^1$ and $R^2$ may form together a divalent hydrocarbon group, $R^1$-$R^2$, having 2 to 10, preferably 2 to 5 carbon atoms.

Examples of the monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched saturated hydrocarbon groups such as an isopropyl group, a 2-isobutyl group, and a 2-methylbutyl group; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and isomers thereof. A part of the hydrogen atoms in the hydrocarbon groups may be substituted with a methyl group or an ethyl group.

The monovalent hydrocarbon group is preferably a methyl group, an ethyl group, an n-propyl group, or an n-butyl group in view of the handling.

Examples of the divalent hydrocarbon group include linear saturated hydrocarbon groups such as an ethylene group, a 1,3-propylene group, and a 1,4-butylene group; branched saturated hydrocarbon groups such as a 1,2-propylene group, a 2,2-dimethyl-1,3-propylene group, a 1,2-butylene group, a 1,3-butylene group, a 2,3-butylene group, and a 2,3-dimethyl-2,3-butylene group; linear unsaturated hydrocarbon groups such as a 1-vinylethylene group; branched unsaturated hydrocarbon groups such as a 2-methylene-1,3-propylene group; cyclic hydrocarbon groups such as a 1,2-cyclopropylene group and a 1,2-cyclobutylene group; and isomers thereof. Apart of the hydrogen atoms in the hydrocarbon groups may be substituted with a methyl group or an ethyl group.

The divalent hydrocarbon group is preferably a lower hydrocarbon group (preferably having 2 to 4 carbon atoms) because these are easily available and highly reactive in the deprotection, and a by-product formed in the deprotection is easily removed by washing or concentration. More preferably, the divalent hydrocarbon group is an ethylene group, a 1,2-propylene group, a 1,3-propylene group, a 1,2-butylene group, a 1,3-butylene group, and a 2,3-dimethyl-2,3-butylene group.

The aryl groups in the triarylphosphonium 9,9-dialkoxynonylide compound (2) represents an aryl group may be same with or different from each other.

The aryl group preferably has 6 to 24, more preferably 6 to 12, even more preferably 6 to 7, carbon atoms.

Examples of the aryl group include a phenyl group (Ph group), a tolyl group, a naphthyl group, and an anthracenyl group. The aryl group is preferably a phenyl group in view of easiness of preparation. More preferably, all of the three aryl groups are a phenyl group.

Examples of the triarylphosphonium 9,9-dialkoxynonylide compound (2) include triphenylphosphonium dialkoxynonylide compounds such as triphenylphosphonium dimethoxynonylide, triphenylphosphonium diethoxynonylide, triphenylphosphonium dipropoxynonylide, triphenylphosphonium dibutoxynonylide, triphenylphosphonium dipentoxynonylide, triphenylphosphonium dihexoxynonylide, triphenylphosphonium diheptoxynonylide, and triphenylphosphonium dioctoxynonylide; and tritolylphosphonium dialkoxynonylide compounds such as tritolylphosphonium dimethoxynonylide, tritolylphosphonium diethoxynonylide, tritolylphosphonium dipropoxynonylide, tritolylphosphonium dibutoxynonylide, tritolylphosphonium dipentoxynonylide, tritolylphosphonium dihexoxynonylide, tritolylphosphonium diheptoxynonylide, and tritolylphosphonium dioctoxynonylide.

The triarylphosphonium 9,9-dialkoxynonylide compound (2) may be used alone or in combination thereof, if necessary.

Next, the triarylphosphonium 9,9-dialkoxynonylide compound (2) may be prepared, for example, by subjecting a 9-halo-1,1-dialkoxynonane compound of the following general formula (5) to a nucleophilic substitution reaction with a phosphorus compound of the following general formula (6) to form a 9,9-dialkoxynonyltriarylphosphonium halide compound of the following general formula (7) and deprotonating the 9,9-dialkoxynonyltriarylphosphonium halide compound (7) in the presence of a base to form the triarylphosphonium 9,9-dialkoxynonylide compound (2).

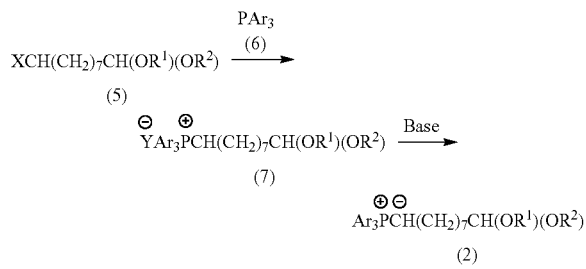

$R^1$ and $R^2$ in the 9-halo-1,1-dialkoxynonane compound (5) are as defined above for the general formula (2).

X in the 9-halo-1,1-dialkoxynonane compound (5) represents a halogen atom such as a chlorine atom, a bromine atom, or an iodine atom. A chlorine atom and a bromine atom are preferred in view of the availability.

Examples of the 9-halo-1,1-dialkoxynonane compound (5) include 9-chloro-1,1-dialkoxynonane compounds such as 9-chloro-1,1-dimethoxynonane, 9-chloro-1,1-diethoxynonane, 9-chloro-1,1-dipropoxynonane, 9-chloro-1,1-dibutoxynonane, 9-chloro-1,1-dipentoxynonane, 9-chloro-1,1-dihexoxynonane, 9-chloro-1,1-diheptoxynonane, and 9-chloro-1,1-dioctoxynonane; 9-bromo-1,1-dialkoxynonane compounds such as 9-bromo-1,1-dimethoxynonane, 9-bromo-1,1-diethoxynonane, 9-bromo-1,1-dipropoxynonane, 9-bromo-1,1-dibutoxynonane, 9-bromo-1,1-dipentoxynonane, 9-bromo-1,1-dihexoxynonane, 9-bromo-1,1-diheptoxynonane, and 9-bromo-1,1-dioctoxynonane; and 9-iodo-1,1-dialkoxynonane compounds such as 9-iodo-1,1-dimethoxynonane, 9-iodo-1,1-diethoxynonane, 9-iodo-1,1-dipropoxynonane, 9-iodo-1,1-dibutoxynonane, 9-iodo-1,1-dipentoxynonane, 9-iodo-1,1-dihexoxynonane, 9-iodo-1,1-diheptoxynonane, and 9-iodo-1,1-dioctoxynonane.

The 9-halo-1,1-dialkoxynonane compound (5) may be obtained by subjecting a 9-halo-1,1-dialkoxynonyne compound or a 9-halo-1,1-dialkoxynonene compound to catalytic hydrogenation. Alternatively, the 9-halo-1,1-dialkoxynonane compound (5) may be also obtained by subjecting 9-chlorononanal to acetalization.

Ar in the phosphorus compound (6) is as defined for the general formula (2).

Examples of the phosphorus compound (6) include triarylphosphine compounds such as triphenylphosphine, tritolylphosphine, trinaphthylphosphine, and trianthracenylphosphine. Triphenylphosphine is preferred in view of the reactivity.

An amount of the phosphorus compound (6) is preferably 0.8 to 5.0 mol per mol of the 9-halo-1,1-dialkoxynonane compound (5) in view of the reactivity.

A halide may be added in the preparation of the 9,9-dialkoxynonyltriarylphosphonium halide compound (7), if necessary.

Examples of the halide include iodides such as sodium iodide and potassium iodide; and bromides such as sodium bromide and potassium bromide. Iodides such as sodium iodide and potassium iodide are preferred in view of the reactivity.

The halide may be used alone or in combination thereof, if necessary. The halide may be commercially available one.

An amount of the halide used is preferably 0.1 to 5.0 mol per mol of the 9-halo-1,1-dialkoxynonane compound (5) in view of the reactivity.

A base may be added in the preparation of the 9,9-dialkoxynonyltriarylphosphonium halide compound (7), if necessary.

Examples of the base include alkaline metal carbonates such as potassium carbonate and sodium carbonate; alkaline earth metal carbonates such as calcium carbonate and magnesium carbonate; and amines such as triethylamine, tripropylamine, triisopropylamine, tributylamine, N,N-diethylaniline, and pyridine. Alkaline metal carbonates are preferred in view of the handling.

The base may be used alone or in combination thereof, if necessary. The base may be commercially available one.

An amount of the base is preferably 0.001 to 1.0 mol per mol of the 9-halo-1,1-dialkoxynonane compound (5) in view of the reactivity.

A reaction temperature in the preparation of the 9,9-dialkoxynonyltriarylphosphonium halide compound (7) varies, depending on a solvent to be used, and is preferably 60 to 180° C.

A reaction time in the preparation of the 9,9-dialkoxynonyltriarylphosphonium halide compound (7) varies, depending on a solvent and/or a reaction scale to be used, and is preferably 1 to 100 hours.

$R^1$ and $R^2$ in the 9,9-dialkoxynonyltriarylphosphonium halide compound (7) are as defined for the general formula (2).

Y in the 9,9-dialkoxynonyltriarylphosphonium halide compound (7) represents a halogen atom such as a chlorine atom, a bromine atom, or an iodine atom.

When the 9,9-dialkoxynonyltriarylphosphonium halide compound (7) is prepared without the halide, Y is the same halogen atom as X is. When the 9,9-dialkoxynonyltriarylphosphonium halide compound (7) is prepared in the presence of an iodide as the halide, Y is the same halogen atom as X is or is an iodine atom.

Ar in the 9,9-dialkoxynonyltriarylphosphonium halide compound (7) represents an aryl group. Ar is as defined for the triarylphosphonium 9,9-dialkoxynonylide compound (2).

Specific examples of the 9,9-dialkoxynonyltriarylphosphonium halide compound (7) include 9,9-dialkoxynonyltriphenylphosphonium chloride compounds such as 9,9-dimethoxynonyltriphenylphosphonium chloride, 9,9-diethoxynonyltriphenylphosphonium chloride, 9,9-dipropoxynonyltriphenylphosphonium chloride, and 9,9-dibutoxynonyltriphenylphosphonium chloride; 9,9- dialkoxynonyltriphenylphosphonium bromide compounds such as 9,9-dimethoxynonyltriphenylphosphonium bromide, 9,9-diethoxynonyltriphenylphosphonium bromide, 9,9-dipropoxynonyltriphenylphosphonium bromide, and 9,9-dibutoxynonyltriphenylphosphonium bromide; 9,9-dialkoxynonyltriphenylphosphonium iodide compounds such as 9,9-dimethoxynonyltriphenylphosphonium iodide, 9,9-diethoxynonyltriphenylphosphonium iodide, 9,9-dipropoxynonyltriphenylphosphonium iodide, and 9,9-dibutoxynonyltriphenylphosphonium iodide; 9,9-dialkoxynonyltritolylphosphonium chloride compounds such as 9,9-dimethoxynonyltritolylphosphonium chloride, 9,9-diethoxynonyltritolylphosphonium chloride, 9,9-dipropoxynonyltritolylphosphonium chloride, and 9,9-dibutoxynonyltritolylphosphonium chloride; 9,9-dialkoxynonyltritolylphosphonium bromide compounds such as 9,9-dimethoxynonyltritolylphosphonium bromide, 9,9-diethoxynonyltritolylphosphonium bromide, 9,9-dipropoxynonyltritolylphosphonium bromide, and 9,9-dibutoxynonyltritolylphosphonium bromide; and 9,9-dialkoxynonyltritolylphosphonium iodide compounds such as 9,9-dimethoxynonyltritolylphosphonium iodide, 9,9-diethoxynonyltritolylphosphonium iodide, 9,9-dipropoxynonyltritolylphosphonium iodide, and 9,9-dibutoxynonyltritolylphosphonium iodide.

The triarylphosphonium 9,9-dialkoxynonylide compound (2) may be obtained by deprotonating the thus-prepared 9,9-dialkoxynonyltriarylphosphonium halide compound (7) in the presence of a base.

The triarylphosphonium 9,9-dialkoxynonylide compound (2) may be directly prepared by adding a base to the reaction mixture obtained in the preparation of the 9,9-dialkoxynonyltriarylphosphonium halide (7). Alternatively, the 9,9-dialkoxynonyltriarylphosphonium halide (7) is isolated from the reaction mixture and purified, and then deprotonated in the presence of a base.

Examples of the base used in the preparation of the triarylphosphonium 9,9-dialkoxynonylide compound (2) include alkyllithium such as n-butyllithium and tert-butyllithium; organometallic reagents such as methylmagnesium chloride, methylmagnesium bromide, sodium acetylide, and potassium acetylide; metal alkoxides such as potassium tert-butoxide, sodium tert-butoxide, potassium methoxide, sodium methoxide, potassium ethoxide, and sodium ethoxide; and metal amides such as lithium diisopropylamide and sodium bis(trimethylsilyl)amide. In view of the reactivity, metal alkoxides are preferred, and potassium tert-butoxide, sodium methoxide, and sodium ethoxide are more preferred.

An amount of the base is preferably 0.7 to 5.0 mol per mol of the 9-halo-1,1-dialkoxynonane compound (5) in view of the reactivity.

A reaction temperature in the preparation of the triarylphosphonium 9,9-dialkoxynonylide compound (2) varies, depending on a solvent and/or a base to be used, and is preferably −78 to 70° C. For example, an optimal temperature in the preparation is −78 to 15° C. when a metal alkoxide is used as the base.

A reaction time in the preparation of the triarylphosphonium 9,9-dialkoxynonylide compound (2) varies, depending on a solvent and/or a reaction scale to be used, and is preferably 0.5 to 100 hours.

A solvent may be used in the preparation of the 9,9-dialkoxynonyltriarylphosphonium halide compound (7) and triarylphosphonium 9,9-dialkoxynonylide compound (2), if necessary.

Example of the solvent include ether solvents such as tetrahydrofuran, diethyl ether, dibutyl ether, 4-methyltetrahydropyran, cyclopentylmethylether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and 4-methyltetrahydropyran, and polar solvents such as acetonitrile, N,N-dimethylformamide, and N,N-dimethylacetamide are preferred in view of the reactivity.

The solvent may be used alone or in combination thereof, if necessary. The solvent may be commercially available one.

An amount of the solvent is preferably 50 to 5000 g per mol of the 9-halo-1,1-dialkoxynonane compound (5) or 9,9-dialkoxynonyltriarylphosphonium halide compound (7) in view of the reactivity.

Wittig Reaction

An amount of the triarylphosphonium 9,9-dialkoxynonylide compound (2) is preferably 1.0 to 4.0 mol, more preferably 1.0 to 2.0 mol, per mol of the (2E)-2-heptenal (1) in view of the reactivity.

A solvent may be used in the Wittig reaction, if necessary. Examples of the solvent include ether solvents such as tetrahydrofuran, diethyl ether, dibutyl ether, 4-methyltetrahydropyran, cyclopentylmethylether, and 1,4-dioxane; hydrocarbon solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and 4-methyltetrahydropyran; and polar solvents such as acetonitrile, N,N-dimethylformamide, and N,N-dimethylacetamide are preferred in view of the reactivity.

The solvent may be used alone or in combination thereof, if necessary. The solvent may be commercially available one.

An amount of the solvent is preferably 50 to 5000 g per mol of the (2E)-2-heptenal (1) in view of the reactivity.

A reaction temperature in the Wittig reaction varies, depending on a solvent to be used, and is preferably −78 to 80° C. The Wittig reaction is more preferably carried out at −78 to 30° C. to carry out the Wittig reaction in a Z-selective manner. The Wittig reaction may be also carried out in an E-selective manner by causing the Wittig reaction at −78 to −40° C. and then processing the resulting intermediate with a strong base such as phenyllithium, i.e., in modified Schlosser manner.

A reaction time in the Wittig reaction varies, depending on a reaction scale, and is preferably 0 to 100 hours.

(5E,7Z)-16,16-Dialkoxy-5,7-Hexadecadiene Compound

The (5E,7Z)-16,16-dialkoxy-5,7-hexadecadiene compound (3) will be explained below.

(3)

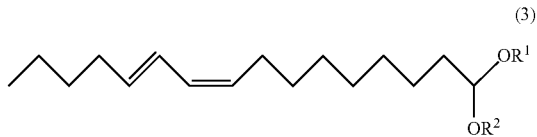

$R^1$ and $R^2$ in the general formula (3) of the (5E,7Z)-16,16-dialkoxy-5,7-hexadecadiene compound are as defined for the general formula (2).

Examples of the (5E,7Z)-16,16-dialkoxy-5,7-hexadecadiene compound (3) include (5E,7Z)-16,16-dimethoxy-5,7-hexadecadiene, (5E,7Z)-16,16-diethoxy-5,7-hexadecadiene, (5E,7Z)-16,16-dipropoxy-5,7-hexadecadiene, (5E,7Z)-16,16-dibutoxy-5,7-hexadecadiene, (5E,7Z)-16,16-dipentoxy-5,7-hexadecadiene, (5E,7Z)-16,16-dihexoxy-5,7-hexadecadiene, (5E,7Z)-16,16-diheptoxy-5,7-hexadecadiene, and (5E,7Z)-16,16-dioctoxy-5,7-hexadecadiene.

II. Preparation of (9Z,11E)-9,11-Hexadecadienal (4)

The target compound of the present invention, (9Z,11E)-9,11-hexadecadienal (4), may be prepared by hydrolyzing the (5E,7Z)-16,16-dialkoxy-5,7-hexadecadiene compound (3), as shown in the following chemical reaction formula.

Hydrolysis Reaction

In one embodiment of the hydrolysis reaction, the (5E,7Z)-16,16-dialkoxy-5,7-hexadecadiene compound (3) may be used alone or, alternatively, a mixture of different (5E,7Z)-16,16-dialkoxy-5,7-hexadecadiene compounds (3) may be used.

In another embodiment of the hydrolysis reaction, when a mixture of a (5E,7Z)-16,16-dialkoxy-5,7-hexadecadiene compound with a (5E,7E)-16,16-dialkoxy-5,7-hexadecadiene compound is used, a mixture of (9Z,11E)-9,11-hexadecadienal and (9E,11E)-9,11-hexadecadienal is obtained.

The hydrolysis reaction may be carried out in the presence of an acid and water.

Examples of the acid include inorganic acids such as hydrochloric acid and hydrobromic acid; p-toluenesulfonic acid, benzenesulfonic acid, trifluoroacetic acid, acetic acid, formic acid, oxalic acid, iodotrimethylsilane, and titanium tetrachloride. Acetic acid, formic acid, and oxalic acid are preferred in view of the reactivity.

The acid may be used alone or in combination thereof, if necessary. The acid may be commercially available one.

An amount of the acid is preferably 0.01 to 10.0 mol per mol of the (5E,7Z)-16,16-dialkoxy-5,7-hexadecadiene compound (3).

An amount of water is preferably 18 to 3000 g per mol of the (5E,7Z)-16,16-dialkoxy-5,7-hexadecadiene compound (3) in view of the reactivity.

A solvent may be further added together with the acid or water in the hydrolysis reaction, if necessary.

Examples of the solvent include hydrocarbon solvents such as toluene, xylene, hexane, heptane, benzene, and cumene; ether solvents such as tetrahydrofuran, diethyl ether, dibutyl ether, 4-methyltetrahydropyran, cyclopentylmethylether, and 1,4-dioxane; polar solvents such as N,N-dimethylformamide, N,N-dimethylacetamide, N-methylpyrrolidone, dimethyl sulfoxide, acetonitrile, acetone, γ-butyrolactone, dichloromethane, and chloroform; and alcohol solvents such as methanol and ethanol.

The solvent may be used alone or in combination thereof, if necessary. The solvent may be commercially available one.

An optimal solvent varies, depending on an acid to be used. For example, when oxalic acid is used as an acid, tetrahydrofuran, acetone, and γ-butyrolactone are preferred in view of the reactivity.

An amount of the solvent used is preferably 0 to 3000 g per mol of the (5E,7Z)-16,16-dialkoxy-5,7-hexadecadiene compound (3) in view of the reactivity.

A reaction temperature of the hydrolysis reaction varies, depending on an acid and/or a solvent to be used, and is preferably 5 to 180° C. in view of the reactivity.

A reaction time of the hydrolysis reaction varies, depending on an acid, a solvent, and/or a reaction scale to be used, and is preferably 1 to 100 hours in view of the reactivity.

EXAMPLES

The present invention will be described with reference to the following Examples. It should be noted that the present invention is not limited to or by the Examples.

The term "purity" as used herein means an area percentage in gas chromatography (GC), unless otherwise specified. The term "production ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-5, 0.25 mm×0.25 mmϕ×30 m; carrier gas: He (1.55 mL/min), detector: FID; column temperature: 150° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

THF represents tetrahydrofuran, $^t$Bu represents a tert-butyl group, and Ph represents a phenyl group.

Example 1: Preparation of (5E,7Z)-16,16-diethoxy-5,7-hexadecadiene (3: $R^1$=CH$_2$CH$_3$, $R^2$=CH$_2$CH$_3$)

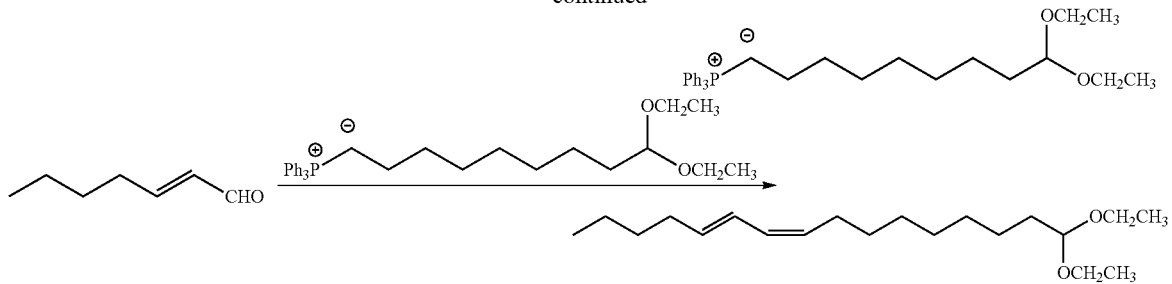

9-Chloro-1,1-diethoxynonane (5: X=Cl; R$^1$=CH$_2$CH$_3$, R$^2$=CH$_2$CH$_3$) (300.97 g, 1.20 mol), triphenylphosphine (6: Ar=Ph) (315.50 g, 1.20 mol), sodium iodide (194.86 g, 1.30 mol), potassium carbonate (9.67 g, 0.07 mol), and acetonitrile (450.00 g) were placed in a reactor at room temperature and stirred at 75 to 85° C. for 15.5 hours to prepare 9,9-diethoxynonyltriphenylphosphonium iodide (7: Y=I; Ar=Ph; R$^1$=CH$_2$CH$_3$, R$^2$=CH$_2$CH$_3$). Next, tetrahydrofuran (800.00 g) was added dropwise to the reactor at 30 to 40° C. After the completion of the dropwise addition, the reaction mixture was cooled to −5 to 10° C. Subsequently, potassium t-butoxide (129.04 g, 1.15 mol) was added and then stirred for 1 hour to prepare triphenylphosphonium 9,9-diethoxynonylide (2: Ar=Ph; R$^1$=CH$_2$CH$_3$, R$^2$=CH$_2$CH$_3$).

Then, (2E)-2-heptenal (1) (120.50 g, 1.00 mol, purity 93.09%, 2E:2Z=99.0:1.0) was added dropwise at −70 to −60° C. After the completion of the dropwise addition, the reaction mixture was stirred at 20 to 30° C. for 12 hours. A mixture of sodium chloride (151.57 g) and water (1515.50 g) was then added to the reaction mixture, followed by phase separation. The aqueous phase was removed to obtain the organic phase. The organic phase was concentrated at a reduced pressure to obtain a crude product, (5E,7Z)-16,16-diethoxy-5,7-hexadecadiene (3: R$^1$=CH$_2$CH$_3$, R$^2$=CH$_2$CH$_3$) (275.15 g, 0.82 mol, purity 92.37%, 5Z7E: 5E7Z:5E7E:5Z7Z=0.4:90.5:8.3:0.8) in a crude yield of 81.85%. Position 5 of (5E,7Z)-16,16-diethoxy-5,7-hexadecadiene (3: R$^1$=CH$_2$CH$_3$, R$^2$=CH$_2$CH$_3$), which was derived from the carbon-carbon double bond of (2E)-2-heptenal, maintained the E conformation. A ratio, 5E:5Z, was 98.8:1.2. The crude product, (5E,7Z)-16,16-diethoxy-5,7-hexadecadiene (3: R$^1$=CH$_2$CH$_3$, R$^2$=CH$_2$CH$_3$), contained triphenylphosphine (6: Ar=Ph) and triphenylphosphine oxide as impurities.

The following are spectrum data of (5E,7Z)-16,16-diethoxy-5,7-hexadecadiene (3: R$^1$=CH$_2$CH$_3$, R$^2$=CH$_2$CH$_3$) thus prepared.

Nuclear magnetic resonance spectrum: $^1$H-NMR (500 MHz, CDCl$_3$): δ=0.89 (3H, t, J=7.3 Hz), 1.20 (6H, t, J=7.3 Hz), 1.25-1.41 (14H, m), 1.56-1.63 (2H, m), 2.09 (2H, dt, J=6.9 Hz, 6.9 Hz), 2.14 (2H, dt, J=6.5 Hz, 6.5 Hz), 3.48 (2H, dq, J=9.4 Hz, 7.2 Hz), 3.63 (2H, dq, J=9.4 Hz, 7.3 Hz), 4.47 (1H, t, J=5.7 Hz), 5.28 (1H, dt, J=10.9 Hz, 7.6 Hz), 5.64 (1H, dt, J=14.5 Hz, 6.9 Hz), 5.93 (1H, dd, J=11.0 Hz, 11.0 Hz), 6.28 (1H, dddt, J=14.9 Hz, 10.9 Hz, 1.2 Hz, 1.2 Hz); $^{13}$C-NMR (500 MHz, CDCl$_3$): δ=13.91, 15.33, 22.25, 24.72, 27.64, 29.15, 29.40, 29.67, 31.53, 32.53, 33.55, 60.77, 102.92, 125.57, 128.57, 129.99, 134.61.

Mass spectrum: EI-mass spectrum (70 eV): m/z 309 (M$^+$−1), 264, 220, 193, 137, 121, 103, 85, 67, 47.

Infrared absorption spectrum (NaCl): νmax=2974, 2926, 2856, 1458, 1374, 1128, 1063, 982, 947, 729.

Example 2: Preparation of (9Z,11E)-9,11-Hexadecadienal (4)

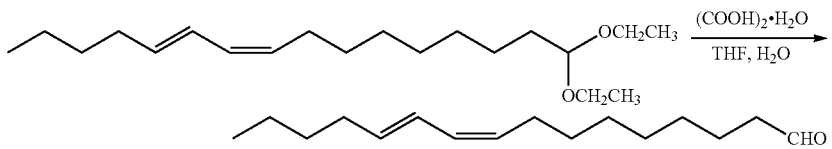

The crude product, (5E,7Z)-16,16-diethoxy-5,7-hexadecadiene (3: R$^1$=CH$_2$CH$_3$, R$^2$=CH$_2$CH$_3$) (275.15 g, 0.82 mol, purity 92.37%, 5Z7E:5E7Z:5E7E:5Z7Z=0.4:90.5:8.3: 0.8), obtained in Example 1, oxalic acid dihydrate (305.86 g, 2.43 mol), tetrahydrofuran (808.70 g), and pure water (808.70 g) were placed in a reactor and stirred at 60 to 65° C. for 3 hours. The reaction mixture was then cooled to 50° C., and hexane (247.84 g) was added and stirred for 30 minutes. After the completion of the stirring, the reaction mixture was left to stand, followed by phase separation. The aqueous phase was removed to obtain the organic phase. The organic phase was concentrated at a reduced pressure, and the concentrate was subjected to distillation at a reduced pressure (140.5 to 143.8° C./0.40 kPa (3.0 mmHg)) to obtain (9Z,11E)-9,11-hexadecadienal (4) (165.05 g, 0.68 mol, purity 98.08%, 9E11Z:9Z11E:9E11E:9Z11Z=0.4:90.6:8.2: 0.8) in an over-all yield of 68.48% in the two steps. Position 11 of (9Z,11E)-9,11-hexadecadienal, which was derived from the carbon-carbon double bond of (2E)-2-heptenal, maintained the E conformation. A ratio, 11E:11Z, was 98.8:1.2.

The following are spectrum data of (9Z,11E)-9,11-hexadecadienal (4) thus prepared.

Nuclear magnetic resonance spectrum: $^1$H-NMR (500 MHz, CDCl$_3$): δ=0.89 (3H, t, J=7.3 Hz), 1.26-1.40 (14H, m), 1.62 (2H, quin-like, J=7.3 Hz), 2.09 (2H, dt, J=6.9 Hz, 6.9 Hz), 2.14 (2H, dt, J=7.1 Hz, 7.1 Hz), 2.41 (2H, dt, J=1.9 Hz, 7.3 Hz), 5.27 (1H, dt, J=10.9 Hz, 7.6 Hz), 5.65 (1H, dt, J=7.3 Hz, 7.3 Hz), 5.93 (1H, dd, J=11.1 Hz, 11.1 Hz), 6.28 (1H, dddt, J=14.9 Hz, 11.1 Hz, 1.2 Hz, 1.2 Hz), 9.75 (1H, t, J=1.9 Hz); $^{13}$C-NMR (500 MHz, CDCl$_3$): δ=13.90, 22.01, 22.23, 27.57, 28.95, 29.07, 29.17, 29.58, 31.51, 32.52, 43.85, 125.52, 128.68, 129.79, 134.70, 202.82.

Mass spectrum: EI-mass spectrum (70 eV): m/z 236 (M$^+$), 221, 207, 193, 179, 165, 151, 135, 123, 109, 95, 81, 67, 55, 41.

Infrared absorption spectrum (NaCl): νmax=2927, 2855, 1727, 1465, 983, 949, 730.

The invention claimed is:

1. A process for preparing (9Z,11E)-9,11-hexadecadienal of the following formula (4):

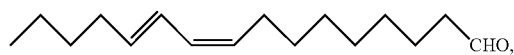
(4)

the process comprising:
subjecting (2E)-2-heptenal of the following formula (1):

(1)

to a Wittig reaction with a triarylphosphonium 9,9-dialkoxynonylide compound of the following general formula (2):

Ar$_3$P$^+$C$^-$H(CH$_2$)$_7$CH(OR$^1$)(OR$^2$)   (2)

wherein Ar represents an aryl group that may be same with or different from each other, and R$^1$ and R$^2$ represent, independently of each other, a monovalent hydrocarbon group having 1 to 15 carbon atoms, or R$^1$ and R$^2$ may form together a divalent hydrocarbon group, R$^1$-R$^2$, having 2 to 10 carbon atoms to form a (5E,7Z)-16,16-dialkoxy-5,7-hexadecadiene compound of the following general formula (3):

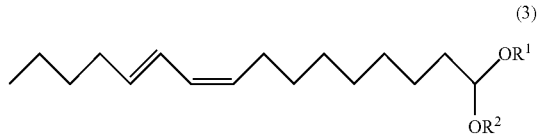
(3)

wherein R$^1$ and R$^2$ are as defined above; and
hydrolyzing the (5E,7Z)-16,16-dialkoxy-5,7-hexadecadiene compound (3) to form (9Z,11E)-9,11-hexadecadienal (4).

2. The process for preparing (9Z,11E)-9,11-hexadecadienal (4) according to claim 1, further comprising
subjecting a 9-halo-1,1-dialkoxynonane compound of the following general formula (5):

X(CH$_2$)$_8$CH(OR$^1$)(OR$^2$)   (5)

wherein X represents a halogen atom, and R$^1$ and R$^2$ are as defined above,
to a nucleophilic substitution reaction with a phosphorus compound of the following general formula (6):

PAr$_3$   (6)

wherein Ar is as defined above,
to form a 9,9-dialkoxynonyltriarylphosphonium halide compound of the following general formula (7):

Y$^-$Ar$_3$P$^+$CH(CH$_2$)$_7$CH(OR$^1$)(OR$^2$)   (7)

wherein Y represents a halogen atom, and Ar, R$^1$ and R$^2$ are as defined above,
and deprotonating the 9,9-dialkoxynonyltriarylphosphonium halide compound (7) in the presence of a base to form the triarylphosphonium 9,9-dialkoxynonylide compound (2).

* * * * *